(12) United States Patent
Wang et al.

(10) Patent No.: US 11,647,898 B2
(45) Date of Patent: May 16, 2023

(54) ENDOSCOPE APPARATUS, MEDICAL DEVICE, AND BELT-LIKE BODY

(71) Applicant: OLYMPUS CORPORATION, Tokyo (JP)

(72) Inventors: Xiongwei Wang, Hino (JP); Tsukasa Ota, Hachioji (JP); Takuto Yoshinaga, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 239 days.

(21) Appl. No.: 16/860,288

(22) Filed: Apr. 28, 2020

(65) Prior Publication Data
US 2020/0253461 A1 Aug. 13, 2020

Related U.S. Application Data

(63) Continuation of application No. PCT/JP2018/031840, filed on Aug. 28, 2018.

(30) Foreign Application Priority Data

Oct. 31, 2017 (JP) .............................. JP2017-210227

(51) Int. Cl.
*A61B 1/012* (2006.01)
*A61B 1/00* (2006.01)
*A61B 1/005* (2006.01)

(52) U.S. Cl.
CPC .......... *A61B 1/0125* (2013.01); *A61B 1/0014* (2013.01); *A61B 1/0052* (2013.01);
(Continued)

(58) Field of Classification Search
CPC .. A61B 1/0125; A61B 1/00128; A61B 1/0014
See application file for complete search history.

(56) References Cited

U.S. PATENT DOCUMENTS 4,502,478 A * 3/1985 Lifton ............... A61M 16/0488
128/207.14
5,584,452 A * 12/1996 Koike ..................... F16L 3/127
248/74.3
(Continued)

FOREIGN PATENT DOCUMENTS

CN 202637329 U 1/2013
EP 2319388 A1 5/2011
(Continued)

OTHER PUBLICATIONS

International Search Report dated Nov. 13, 2018 issued in PCT/JP2018/031840.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope apparatus includes: an endoscope including a first operation portion that is coupled to a first insertion portion to be inserted into a subject; a medical device including a second operation portion that is coupled to a second insertion portion to be inserted into the subject through the first insertion portion, the second operation portion including at least one locking member; and a belt-like body having flexibility and including at least three end portions in which at least one end portion includes a locked portion to be locked to the locking portion, the belt-like body being configured to be wound around the endoscope to hold and fix the second operation portion of the medical device in a state where the at least three end portions are connected to the second operation portion.

8 Claims, 12 Drawing Sheets

(52) U.S. Cl.
CPC ...... *A61B 1/00066* (2013.01); *A61B 1/00121* (2013.01); *A61B 1/00128* (2013.01)

(56) References Cited

U.S. PATENT DOCUMENTS

| | | | | |
|---|---|---|---|---|
| 5,894,840 | A * | 4/1999 | King | A61M 16/0493 128/200.26 |
| 5,957,423 | A * | 9/1999 | Kronner | A61B 90/57 248/278.1 |
| 6,634,359 | B1 * | 10/2003 | Rudy, Jr. | A61M 16/0493 128/207.14 |
| 6,708,838 | B2 * | 3/2004 | Bergman | B65D 25/2829 220/756 |
| 7,179,223 | B2 * | 2/2007 | Motoki | A61B 1/00052 600/102 |
| 7,644,835 | B2 * | 1/2010 | Bergman | B65D 25/28 220/736 |
| 7,922,650 | B2 * | 4/2011 | McWeeney | A61M 25/0068 600/172 |
| 8,028,948 | B1 * | 10/2011 | Holt | A01K 97/00 242/322 |
| 8,353,493 | B2 * | 1/2013 | Golden | A61B 1/00128 248/230.7 |
| 8,608,019 | B2 * | 12/2013 | Wren | A47G 23/0266 220/759 |
| 8,936,549 | B2 * | 1/2015 | Cobb | A61B 17/02 600/210 |
| 9,174,691 | B2 * | 11/2015 | Goldwater | B62J 43/20 |
| 10,085,622 | B2 * | 10/2018 | Walish | A61B 1/307 |
| 10,100,989 | B1 * | 10/2018 | Hamasaki | F21S 41/141 |
| 10,201,264 | B2 * | 2/2019 | Golden | A61B 1/018 |
| 11,229,277 | B1 * | 1/2022 | Davies | A63B 21/4037 |
| 2002/0029399 | A1 * | 3/2002 | Hill | A61F 9/026 2/13 |
| 2004/0015050 | A1 | 1/2004 | Goto et al. | |
| 2004/0116818 | A1 * | 6/2004 | Chen | A61B 5/6831 600/509 |
| 2005/0044673 | A1 * | 3/2005 | Huang | A47G 1/17 24/303 |
| 2005/0272975 | A1 * | 12/2005 | McWeeney | A61B 6/06 600/172 |
| 2006/0030753 | A1 | 2/2006 | Boutillette et al. | |
| 2006/0252993 | A1 * | 11/2006 | Freed | A61B 1/00133 604/95.04 |
| 2007/0248501 | A1 * | 10/2007 | Morgan | A61B 90/50 422/400 |
| 2008/0276492 | A1 * | 11/2008 | Burnett | A43C 11/22 36/51 |
| 2010/0155545 | A1 * | 6/2010 | Birli | F16L 3/13 248/65 |
| 2011/0060187 | A1 * | 3/2011 | Belafsky | A61B 1/018 600/104 |
| 2011/0099773 | A1 * | 5/2011 | Golden | F16B 2/12 24/457 |
| 2012/0172850 | A1 * | 7/2012 | Kappel | A61B 1/00149 606/1 |
| 2012/0182748 | A1 * | 7/2012 | McCaslin | F21V 23/06 362/105 |
| 2013/0205476 | A1 * | 8/2013 | Gentile | A41F 1/08 2/311 |
| 2014/0223701 | A1 * | 8/2014 | Bean | A61B 1/00066 24/483 |
| 2014/0343358 | A1 * | 11/2014 | Hameed | A61B 1/053 600/109 |
| 2015/0069728 | A1 * | 3/2015 | Seitz, III | A61M 25/00 206/305 |
| 2015/0133010 | A1 * | 5/2015 | Donahue | A63B 31/11 441/63 |
| 2015/0150632 | A1 * | 6/2015 | Kappel | A61B 1/00149 600/102 |
| 2015/0217074 | A1 * | 8/2015 | Wells | A61M 16/06 128/207.18 |
| 2015/0230558 | A1 * | 8/2015 | Flores | A43C 1/00 24/72.7 |
| 2016/0089008 | A1 | 3/2016 | Simmons | |
| 2016/0252749 | A1 * | 9/2016 | Necklas | G02C 3/006 351/121 |
| 2017/0156533 | A1 * | 6/2017 | Pajonas | A47G 29/1209 |
| 2017/0188793 | A1 * | 7/2017 | Ouyang | A61B 1/015 |
| 2018/0042603 | A1 * | 2/2018 | Mitelberg | A61B 1/00101 |
| 2019/0191814 | A1 * | 6/2019 | Stuempfig | A43B 3/10 |
| 2020/0178653 | A1 * | 6/2020 | Yoshino | A44B 19/24 |
| 2020/0187856 | A1 * | 6/2020 | Kim | A61B 5/14551 |
| 2020/0214542 | A1 * | 7/2020 | Yoshinaga | A61B 1/0125 |
| 2020/0245853 | A1 * | 8/2020 | Wang | A61B 1/018 |
| 2020/0253461 | A1 * | 8/2020 | Wang | A61B 1/0125 |
| 2022/0030996 | A1 * | 2/2022 | Wenkman | A41F 17/00 |
| 2022/0071482 | A1 * | 3/2022 | Yee | A61B 1/00087 |

FOREIGN PATENT DOCUMENTS

| | | |
|---|---|---|
| JP | H04-124101 U | 11/1992 |
| JP | H06-65682 U | 9/1994 |
| JP | 2007-111541 A | 5/2007 |
| JP | 2007-530155 A | 11/2007 |
| WO | WO 2005/094665 A1 | 10/2005 |
| WO | WO 2016/053754 A1 | 4/2016 |

* cited by examiner

ENDOSCOPE APPARATUS, MEDICAL DEVICE, AND BELT-LIKE BODY

CROSS REFERENCE TO RELATED APPLICATION

This application is a continuation application of PCT/JP2018/031840 filed on Aug. 28, 2018 and claims benefit of Japanese Application No. 2017-210227 filed in Japan on Oct. 31, 2017, the entire contents of which are incorporated herein by this reference.

BACKGROUND OF THE INVENTION

1. Field of the Invention

The present invention relates to an endoscope apparatus including an endoscope and an insertion device used together with the endoscope, a medical device, and a belt-like body.

2. Description of the Related Art

In the related art, an endoscope capable of observing organs in a body cavity by insertion of an elongated insertion portion into the body cavity has been widely used in medical fields.

Such an endoscope is used together with another medical device such as an insertion device according to various procedures and examinations. In an endoscope apparatus including such an endoscope and a medical device, for example, a so-called mother-baby type endoscope has been practically used as an endoscope used for observing or treating the inside of a bile duct or a pancreatic duct.

The mother-baby type endoscope is configured to observe and treat the inside of the bile duct or the pancreatic duct by inserting a small-diameter endoscope serving as a baby endoscope, which is the medical device, into a normal-sized endoscope serving as a mother endoscope, for example, a treatment instrument insertion channel of a duodenoscope.

As for such a conventional mother-baby type endoscope, various types have been proposed, for example, in U.S. Pat. No. 7,922,650 B2 and put into practical use.

A conventional mother-baby type endoscope proposed in U.S. Pat. No. 7,922,650 B2 is configured in which a baby endoscope is fixed to an operation portion of a mother endoscope by a band.

SUMMARY OF THE INVENTION

An endoscope apparatus according to one aspect of the present invention includes: an endoscope including a first operation portion that is coupled to a first insertion portion to be inserted into a subject; a medical device including a second operation portion that is coupled to a second insertion portion to be inserted into the subject through the first insertion portion, the second operation portion including at least one locking member; and a belt-like body having flexibility and including at least three end portions in which at least one end portion includes a locked member to be locked to the locking member, the belt-like body being configured to be wound around the endoscope to hold and fix the second operation portion of the medical device in a state where the at least three end portions are connected to the second operation portion.

A medical device according to another aspect of the present invention includes a device operation portion fixed to an endoscope operation portion provided on an endoscope to be inserted into a subject, the device operation portion being provided with at least one locking member, the medical device including a belt-like body having flexibility and including at least three end portions in which at least one end portion includes a locked member to be locked to the locking member, the belt-like body being configured to be wound around the endoscope to hold and fix the device operation portion to the endoscope in a state where the at least three end portions are connected to the device operation portion.

A belt-like body according to still another aspect of the present invention has elasticity and includes at least three end portions, each of the at least three end portions including a locked member to be locked to an endoscope operation portion.

DETAILED DESCRIPTION OF THE PREFERRED EMBODIMENT(S)

Figure 1:
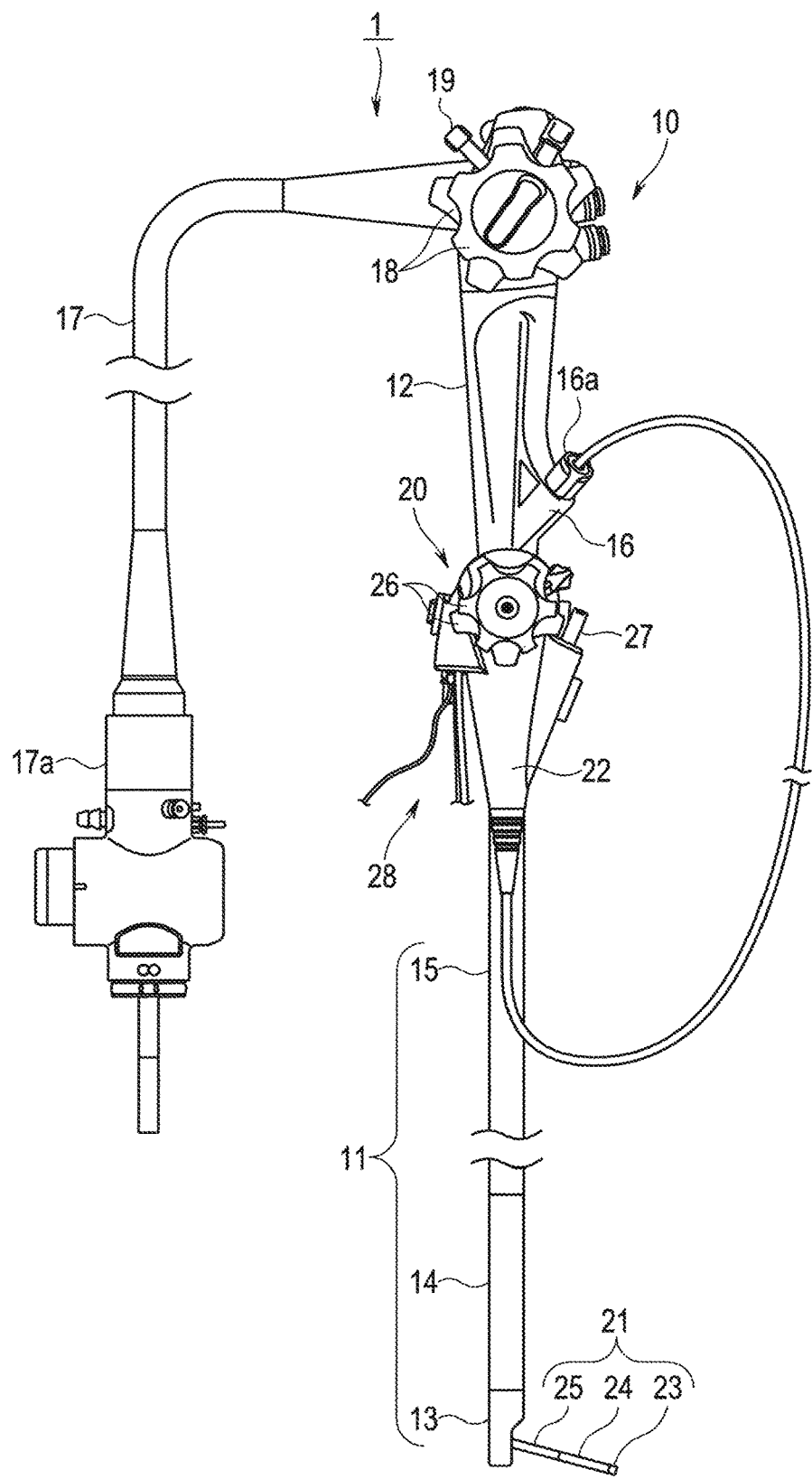
FIG. 1 is a plan view showing a configuration of an endoscope apparatus of an embodiment.

A preferred embodiment of the present invention will be described below with reference to the drawings.

Note that, in each of the drawings used in the following description, scales are varied for each component to show the respective components in recognizable sizes in the drawings. Accordingly, the present invention is not limited only to numbers of the components, shapes of the components, ratios of sizes of the components, and relative positional relations among the respective components shown in the drawings. In the following description, up and down directions viewed from a paper surface of the drawings may sometimes be described as an upper part and a lower part of a component.

Figure 2:
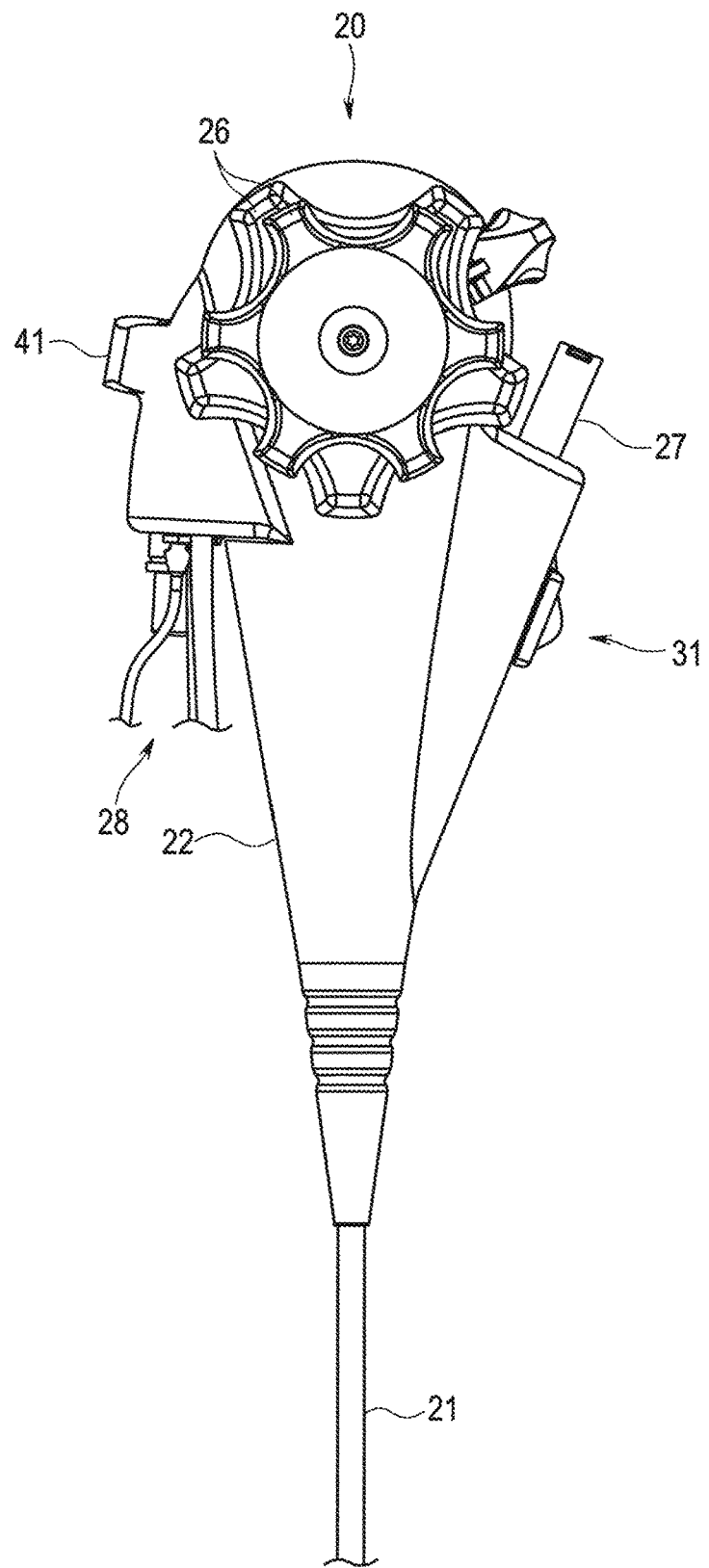
FIG. 2 is a left side view showing a configuration of a baby endoscope of the embodiment.
Figure 3:
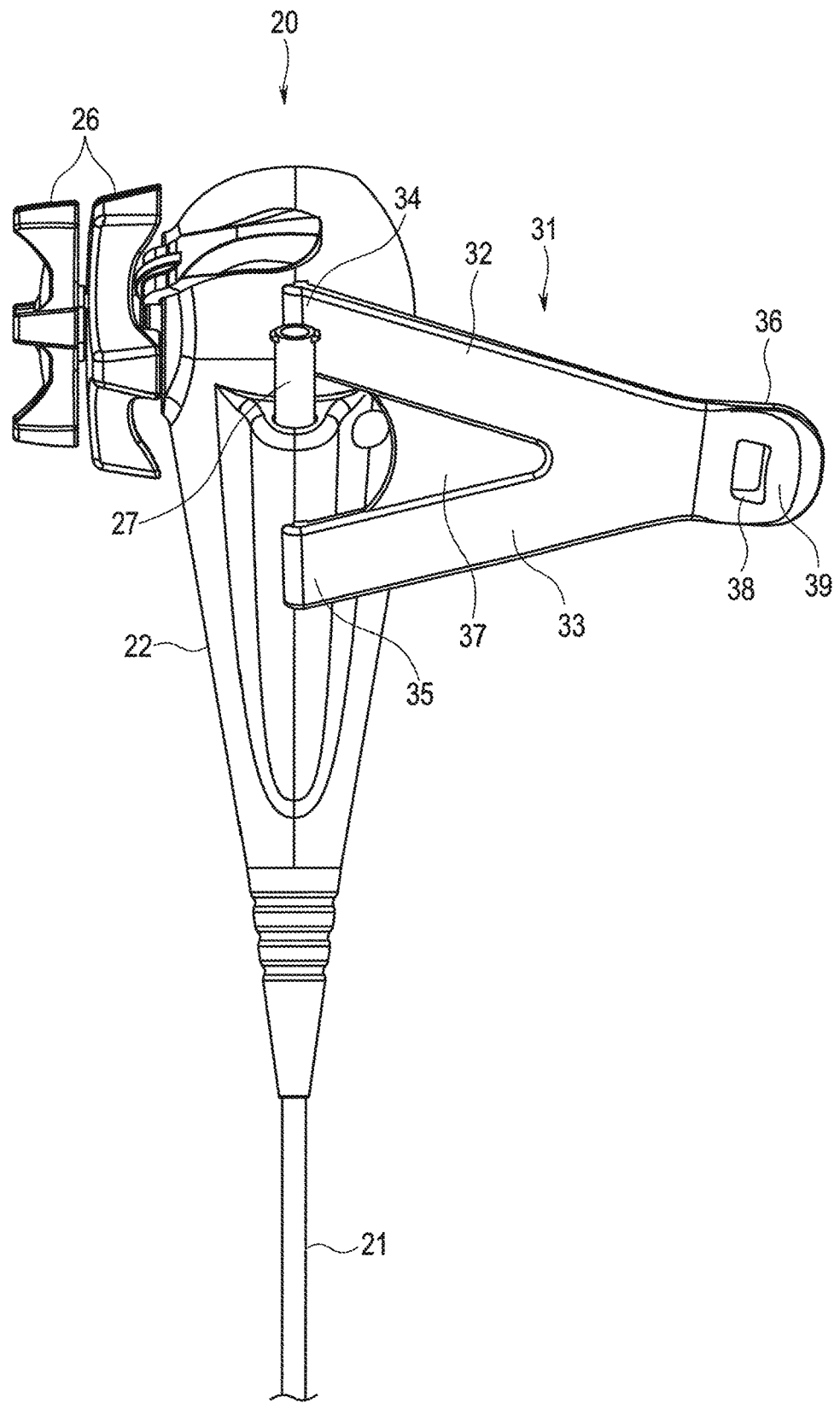
FIG. 3 is a front view showing the configuration of the baby endoscope of the embodiment.
Figure 4:
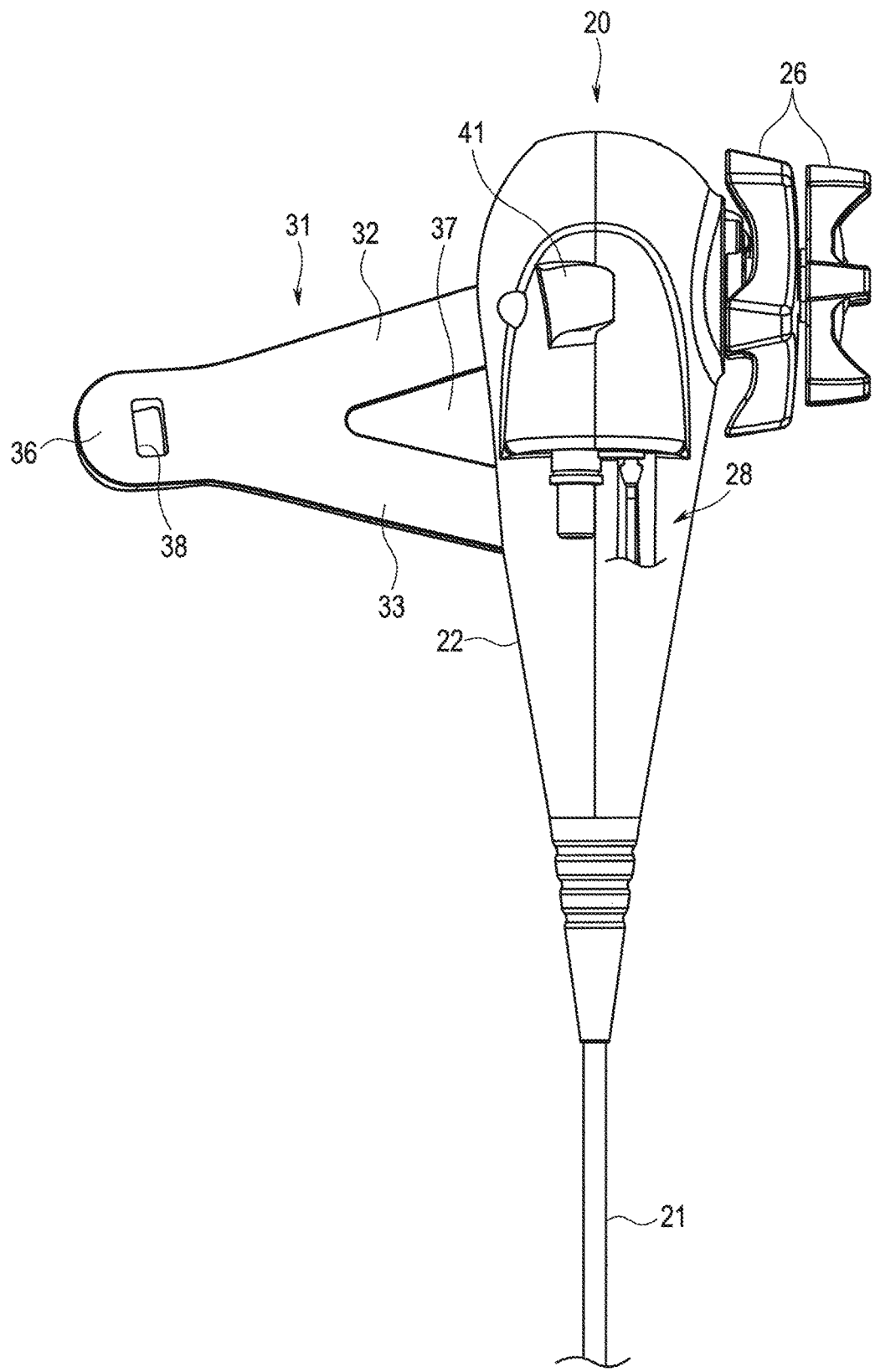
FIG. 4 is a rear view showing the configuration of the baby endoscope of the embodiment.
Figure 5:
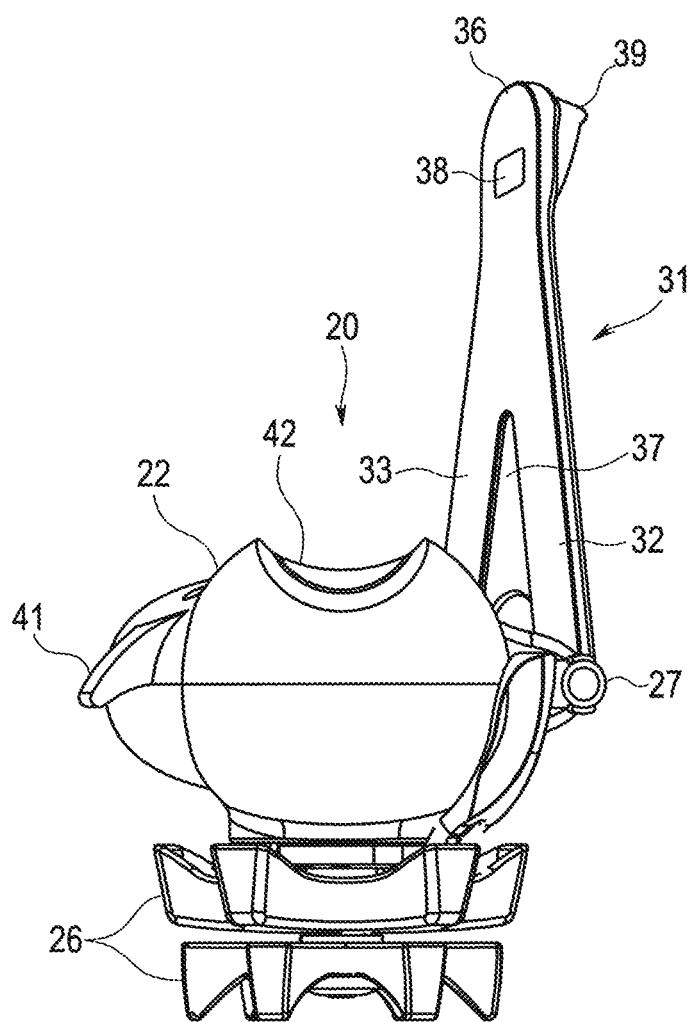
FIG. 5 is a top view showing the configuration of the baby endoscope of the embodiment.
Figure 6:
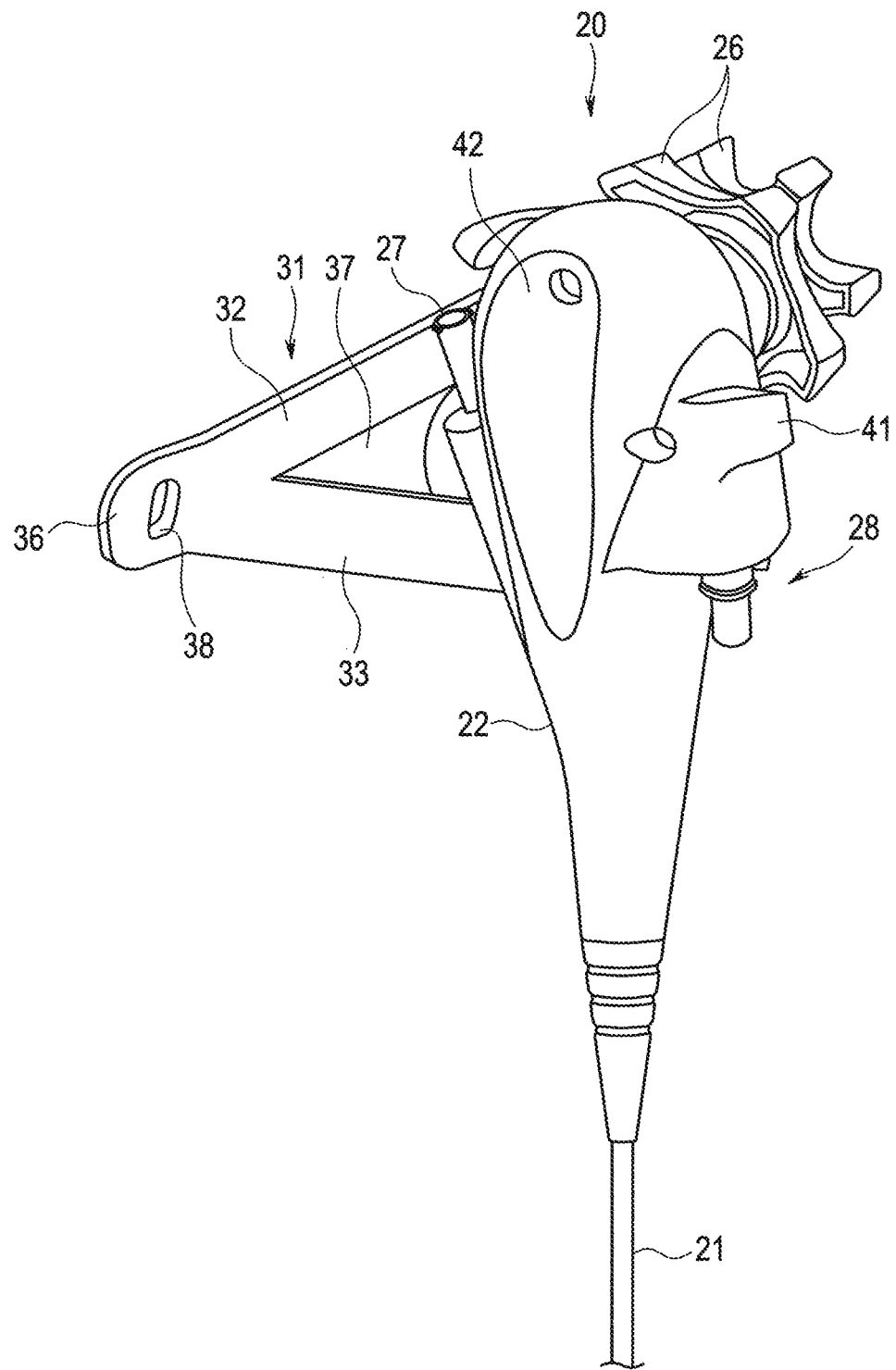
FIG. 6 is a perspective view showing the configuration of the baby endoscope of the embodiment.
Figure 7:
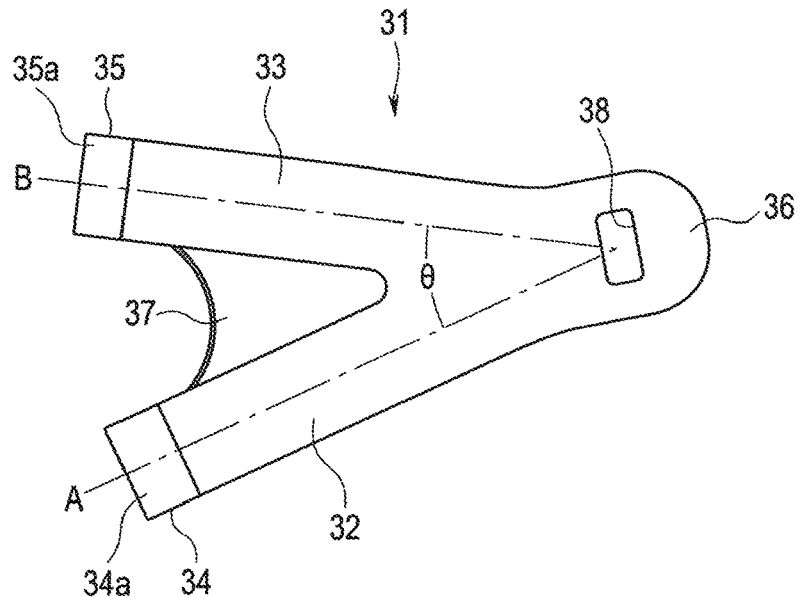
FIG. 7 is a plan view showing a configuration of a fixing band of the embodiment.
Figure 8:
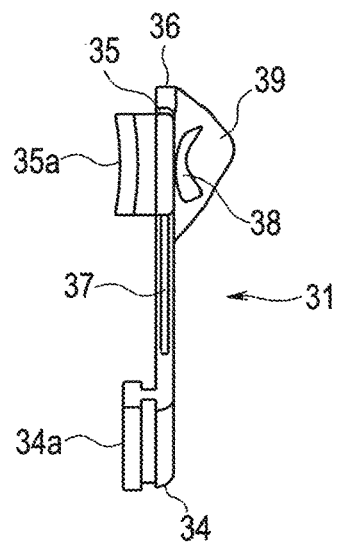
FIG. 8 is a side view showing the configuration of the fixing band of the embodiment.
Figure 9:
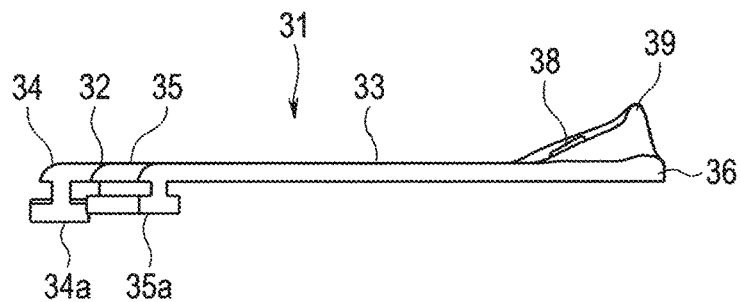
FIG. 9 is a top view showing the configuration of the fixing band of the embodiment.
Figure 10:
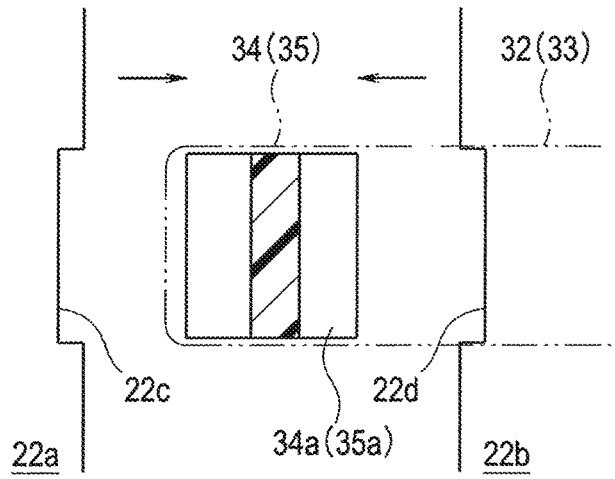
FIG. 10 is a schematic cross-sectional view showing a state where an end portion of the fixing band is not yet fixed to an outer case body of an operation portion of the embodiment.
Figure 11:
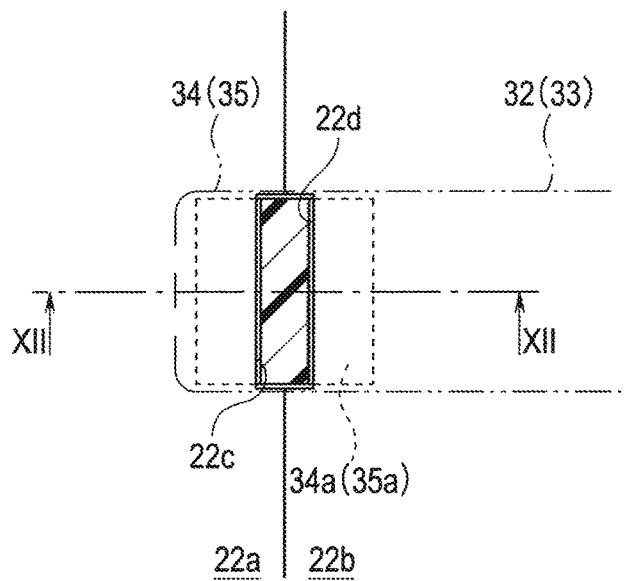
FIG. 11 is a schematic cross-sectional view showing a state where the end portion of the fixing band is fixed to the outer case body of the operation portion of the embodiment.
Figure 12:
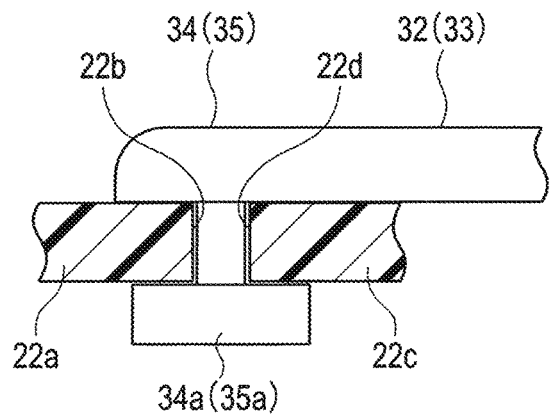
FIG. 12 is a cross-sectional view taken along line XII-XII in FIG. 11 of the embodiment.
Figure 13:
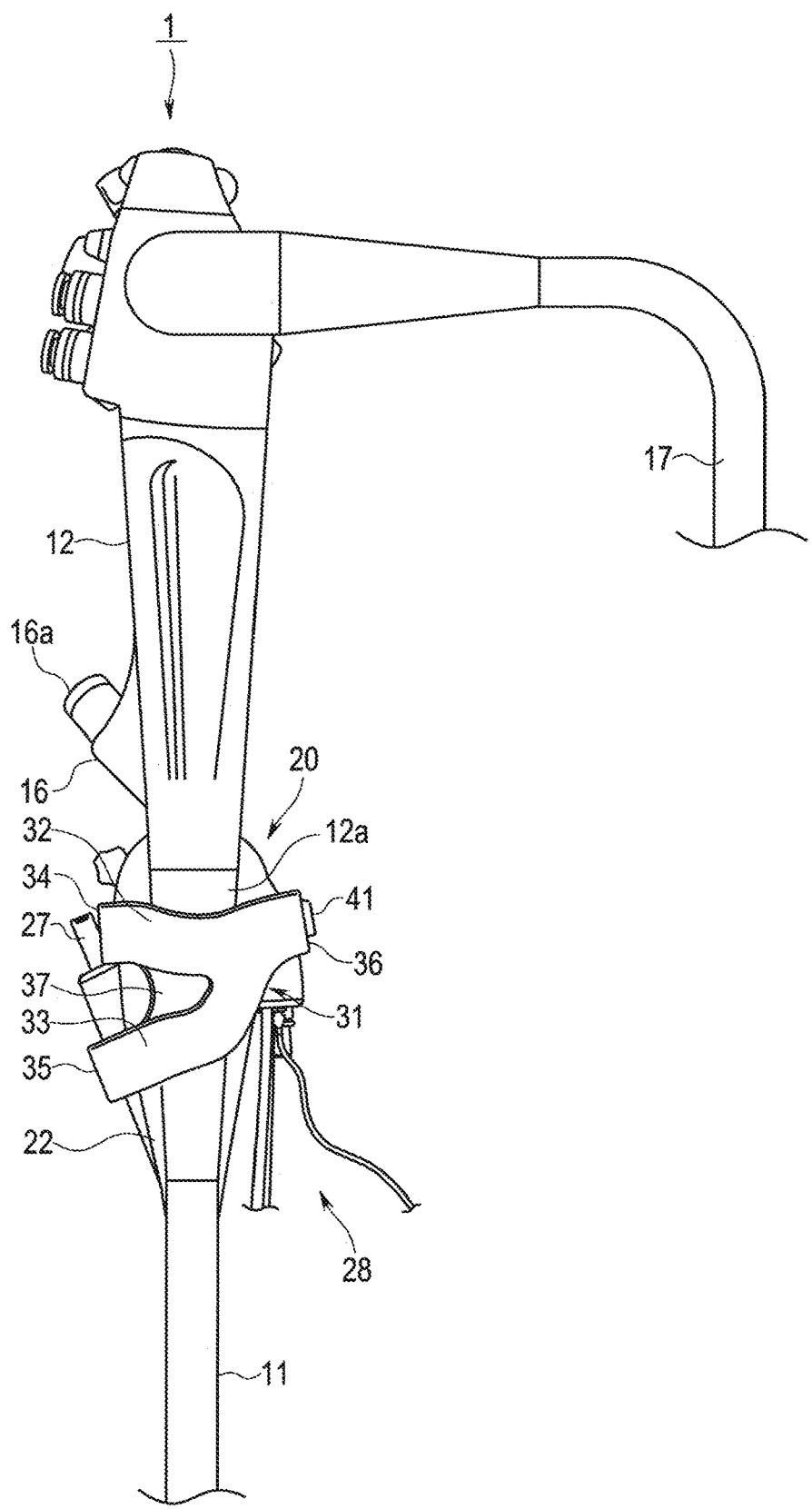
FIG. 13 is a side view of the endoscope apparatus showing a state where the baby endoscope is fixed to a mother endoscope of the embodiment.
Figure 14:
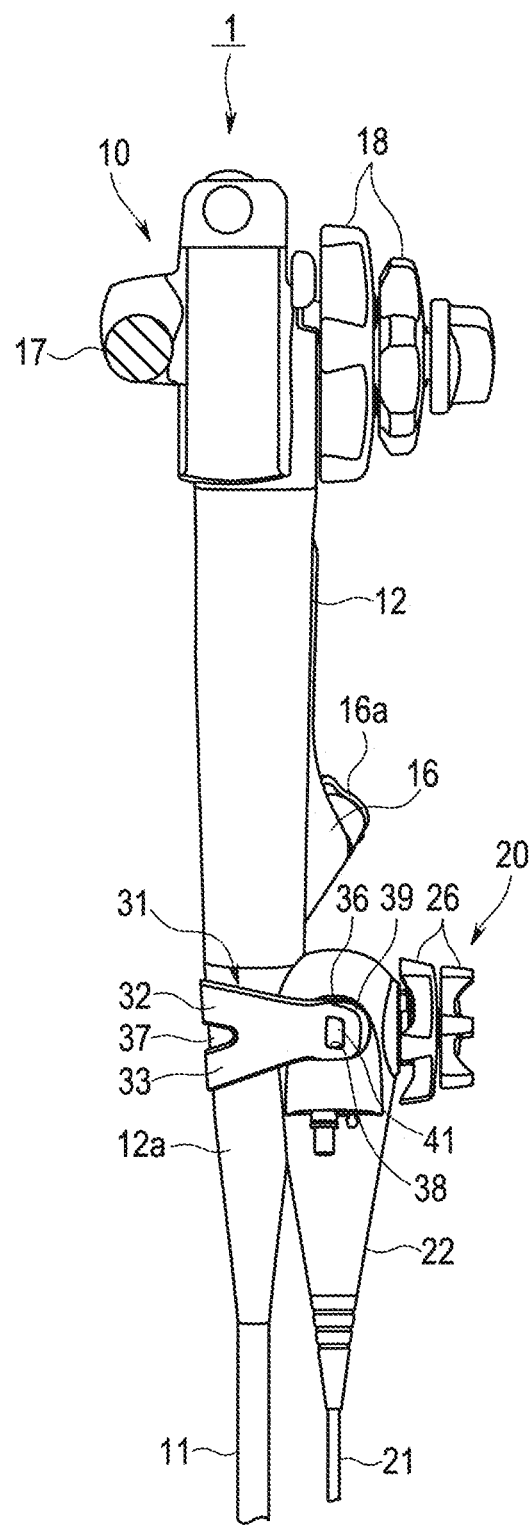
FIG. 14 is a rear view of the endoscope apparatus showing a state where the baby endoscope is fixed to the mother endoscope of the embodiment.

FIG. 1 is a plan view showing a configuration of an endoscope apparatus, FIG. 2 is a left side view showing a configuration of a baby endoscope, FIG. 3 is a front view showing the configuration of the baby endoscope, FIG. 4 is a rear view showing the configuration of the baby endoscope, FIG. 5 is a top view showing the configuration of the baby endoscope, FIG. 6 is a perspective view showing the configuration of the baby endoscope, FIG. 7 is a plan view showing a configuration of a fixing band, FIG. 8 is a side view showing the configuration of the fixing band, FIG. 9 is a top view showing the configuration of the fixing band, FIG. 10 is a schematic cross-sectional view showing a state where an end portion of the fixing band is not fixed to an outer case body of an operation portion, FIG. 11 is a schematic cross-sectional view showing a state where the end portion of the fixing band is fixed to the outer case body of the operation portion, FIG. 12 is a cross-sectional view taken along line XII-XII in FIG. 11, FIG. 13 is a side view of the endoscope apparatus showing a state where the baby endoscope is fixed to a mother endoscope, and FIG. 14 is a rear view of the endoscope apparatus showing a state where the baby endoscope is fixed to the mother endoscope.

First, an endoscope apparatus of the present embodiment will be described below. In addition, the endoscope apparatus described herein exemplifies a mother-baby type endoscope including a mother endoscope and a baby endoscope which is a medical device.

A mother-baby type endoscope 1 serving as the endoscope apparatus of the present embodiment includes a mother endoscope 10 which is an endoscope and a baby endoscope 20 which is a medical device fixed to the mother endoscope 10. Note that the baby endoscope 20 described herein is a disposable medical device that is discarded after use, for example, as an example of the embodiment.

The mother endoscope 10 includes an elongated insertion portion 11 to be inserted into a subject and an operation portion 12 provided with a bend preventing portion 12*a* (which will be described below) through which a proximal end side of the insertion portion 11 is coupled.

The insertion portion 11 is formed to have an outer diameter of about 10 mm and a length of about 1.2 m, and includes a distal end body 13, a bending portion 14, and a flexible tube portion 15 that are continuously connected in this order from the distal end.

A treatment instrument insertion channel, which is a tube channel (not shown), is formed inside the insertion portion 11. The treatment instrument insertion channel is inserted into the distal end body 13 from a treatment instrument insertion portion 16 provided in the operation portion 12. A disposable forceps valve 16*a* is detachably attached to the treatment instrument insertion portion 16.

In addition to the treatment instrument, for example, an insertion portion 21 of the baby endoscope 20 can be inserted into the treatment instrument insertion channel.

Inside the distal end body 13, a treatment instrument inserted through the treatment instrument insertion channel (not shown) and protruding an opening provided on a side of the distal end portion of the treatment instrument insertion channel and a treatment instrument raising base (not shown) for raising the insertion portion 21 and the like of the baby endoscope 20. In other words, the mother endoscope 10 is a side-view/oblique-view type endoscope.

Although not shown herein, an image pickup unit including an objective optical system, an image sensor such as a CCD or a CMOS, and an illumination optical system for irradiating illumination light transmitted by a light guide bundle are provided inside the distal end body 13 of the insertion portion 11 or the operation portion 12.

The operation portion 12 includes, for example, various operation members necessary for operating the mother endoscope 10 and a universal cable 17 that performs connection with an endoscope unit (not shown) that controls the mother endoscope 10. An endoscope coupler 17*a* is provided at an extending end of the universal cable 17 to be detachable from an external device (not shown) such as a light source device.

The flexible tube portion 15 of the insertion portion 11 is configured by a tubular flexible member that is bendable passively. An image pickup cable, a light guide bundle, a treatment instrument insertion channel, and an air/water feeding tube (which are not shown) are inserted into the flexible tube portion 15. As the operation members, the operation portion 12 includes a pair of bending operation knobs 18 that is used to bend the bending portion 14 and an operation lever 19 that is used to lay down and raise the treatment instrument raising base.

The bending portion 14 of the insertion portion 11 is configured to be actively bendable in all circumferential directions around an insertion axis O including up-down/right-left directions in response to a rotation operation input of the pair of bending operation knobs 18 from a user as an operator.

A description will be given in detail below with respect to a configuration of the baby endoscope 20 which is a medical device used with the mother endoscope 10 of the present embodiment.

The baby endoscope 20 shown in FIGS. 1 to 6 includes the elongated insertion portion 21 and an operation portion 22 that is provided continuously on the proximal end of the insertion portion 21.

The insertion portion 21 is formed to have an outer diameter of about 3 to 4 mm and a length of about 2 m, and includes a distal end body 23 arranged with an observation window, an illumination window (not shown), and the like, a bending portion 24, and a flexible tube portion 25 that are continuously connected in this order from the distal end.

As in the mother endoscope 10, although not shown herein, an image pickup unit including an objective optical system, an image sensor such as a CCD or a CMOS, an LED light source for radiating illumination light, and an illumination optical system are provided inside the distal end body 23 of the insertion portion 21 or the operation portion 22.

The operation portion 22 includes a pair of bending operation knobs 26 that is used to bend the bending portion 24 and other various operation members necessary for operating the baby endoscope 20.

In the operation portion 22 of the baby endoscope 20, a hook portion 41 serving as a locking member is provided to lock detachably a fixing band 31 which will be described below, and a concave portion 42 is formed in an exterior part on a side opposite to the pair of bending operation knobs 26 and attached to the operation portion 12 of the mother endoscope 10.

As in the mother endoscope 10, the bending portion 24 of the insertion portion 21 is configured to be actively bendable in all circumferential directions around an insertion axis O including up-down/right-left directions in response to a rotation operation input of the pair of bending operation knobs 26 from a user as an operator.

The insertion portion 21 of the baby endoscope 20 includes a channel (not shown) through which a contrast agent is injected. A distal end of the channel is opened by the distal end body 23, and a proximal end of the channel is opened by a pipe sleeve 27 of the operation portion 22. The hook portion 41 is provided on the exterior part of the operation portion 22 that is separated from the pipe sleeve 27.

In addition, cables/tubes 28, for example, cables for image pickup and power supply, air/water feeding tubes, suction tubes extend from the operation portion 22.

Here, the operation portion 22 of the baby endoscope 20 is provided with a fixing band 31 that is a flexible belt-like body configured to fix the operation portion 12 of the mother endoscope 10 by winding.

The fixing band 31 is formed of a resin such as silicone rubber having a substantially triangular outer shape, for example, a substantially A shape of an alphabet, and has elasticity.

Specifically, as shown in FIG. 7, the fixing band 31 diverges into a first belt-like portion 32 and a second belt-like portion 33 such that an angle between a longitudinal axis A of the first belt-like portion 32 and a longitudinal axis B of the second belt-like portion 33 forms a V-shape (or Y-shape) that is set to a predetermined angle θ, and a joining band 37 having an arc-shaped edge is formed to connect the first belt-like portion 32 and the second belt-like portion 33 that diverge from the fixing band 31.

As shown in FIGS. 8 and 9, an outward flange-shaped locking portion 34a is formed at an end portion 34 of the first belt-like portion 32 separated from the second belt-like portion 33 so as to protrude from one surface. Similarly, an outward flange-shaped locking portion 35a is formed at an end portion 35 of the second belt-like portion 33 separated from the first belt-like portion 32 so as to protrude from one surface.

A hook hole 38 serving as a locking hole, which is a locked member, is formed at an end portion 36 on a joining side of the first belt-like portion 32 and the second belt-like portion 33, and the end portion 36 includes a finger-hook convex portion 39 raised so as to be inclined in a direction away from the end portion 34 of the first belt-like portion 32 and the end portion 35 of the second belt-like portion 33.

As shown in FIGS. 10 to 12, the fixing band 31 described above is configured such that the end portions 34 and 35 of the first belt-like portion 32 and the second belt-like portion 33 are respectively fixed along bonding lines of two outer case bodies 22a and 22b forming an exterior of the operation portion 22 of the baby endoscope 20.

Specifically, rectangular concave portions 22c and 22d are formed at bonding edges of the two outer case bodies 22a and 22b, respectively. Then, the two outer case bodies 22a and 22b are bonded such that the concave portions 22c and 22d are fitted with the locking portions 34a and 35a, respectively, so as to lock the outward flange portions of the first belt-like portion 32 and the second belt-like portion 33 at an inner surface.

Thus, the fixing band 31 is configured such that the respective end portions 34 and 35 of the first belt-like portion 32 and the second belt-like portion 33 are connected to the operation portion 22 of the baby endoscope 20. The fixing band 31 is configured such that the end portion 34 of the first belt-like portion 32 is connected to the operation portion 22 at an upper position of the pipe sleeve 27 and the end portion 35 of the second belt-like portion 33 is connected to the operation portion 22 at a lower position along the pipe sleeve 27. In other words, the fixing band 31 is fixed at two places of the operation portion 22 which are separated by a predetermined distance from each other (see FIG. 3).

In the mother-baby type endoscope 1, which is the endoscope apparatus described above, as shown in FIG. 1, the operation portion 22 of the baby endoscope 20 is attached to the insertion portion 11 located on the distal end side (a lower side in the drawing) from the treatment instrument insertion portion 16 of the operation portion 12 of the mother endoscope 10.

More specifically, as shown in FIGS. 13 and 14, the operation portion 22 of the baby endoscope 20 is held and fixed to the truncated cone-shaped bend preventing portion 12a, which is a coupling portion with the insertion portion 11 provided in the operation portion 12 of the mother endoscope 10, by winding of the fixing band 31.

At this time, the fixing band 31 is connected in a manner that the hook hole 38 serving as the locked portion formed at the end portion 36 on the joining side of the first belt-like portion 32 and the second belt-like portion 33 is hooked and locked to the hook portion 41 serving as the locking portion provided on the operation portion 22 of the baby endoscope 20. In addition, the operation portion 22 of the baby endoscope 20 is fixed to the operation portion 12 of the mother endoscope 10 such that the concave portion 42 (see FIGS. 5 and 6) faces the bend preventing portion 12a.

As described above, the baby endoscope 20 is fixed to the bend preventing portion 12a of the mother endoscope 10 at a total of three places (three points) including the two end portions 34 and 35 of the first belt-like portion 32 and the second belt-like portion 33 separated from each other and the end portion 36 on the joining side of the first belt-like portion 32 and the second belt-like portion 33, by the fixing band 31.

In addition, even when the bend preventing portion 12a has a conical shape in which a diameter becomes smaller from the upper side to the lower side as in the present embodiment, the baby endoscope 20 is stably fixed in a manner that rear surfaces of the first belt-like portion 32 and the second belt-like portion 33 of the fixing band 31 having elasticity closely contact with the surface of the truncated cone-shaped bend preventing portion 12a having different outer diameters.

In other words, since the fixing band 31, which has elasticity and diverges in the V-shape (or Y-shape), is fixed at three places, even when the baby endoscope 20 is fixed to a part such as the bend preventing portion 12a having different diameters of the mother endoscope 10, the fixing band 31 can closely contact with the part having different diameters by a single fixing operation. Thus, attachment is easier and stability is improved compared with a case where the baby endoscope 20 is fixed to the mother endoscope 10 by one or plurality of belt-like bands having a simple linear shape.

Therefore, the baby endoscope 20 is stably fixed to the bend preventing portion 12a without slipping and falling of the operation portion 12 of the mother endoscope 10 from the bend preventing portion 12a, and thus the baby endoscope 20 hardly moves during various operations and is improved in operability.

From the above description, the mother-baby type endoscope 1, which is the endoscope apparatus of the present embodiment has a configuration in which the baby endoscope 20 serving as a medical device can be stably fixed to the operation portion 12 of the mother endoscope 10 by the fixing band 31 and the baby endoscope 20 can be stably fixed without slipping and falling, thereby being improved in operability.

Note that the baby endoscope 20 may be fixed to, for example, the operation portion 12 between the treatment instrument insertion portion 16 and the bending operation knob 18 by the fixing band 31 without being fixed to the bend preventing portion 12a of the operation portion 12 of the mother endoscope 10, or may be fixed to a root part of the insertion portion 11 by the fixing band 31.

Further, the fixing band 31 may be configured to fix the baby endoscope 20 to the mother endoscope 10 at three places (three points) in a manner that one end portion is fixed to the operation portion 22 of the baby endoscope 20 and two end portions are locked to the hook portions 41, respectively.

(First Modification)

Figure 15:
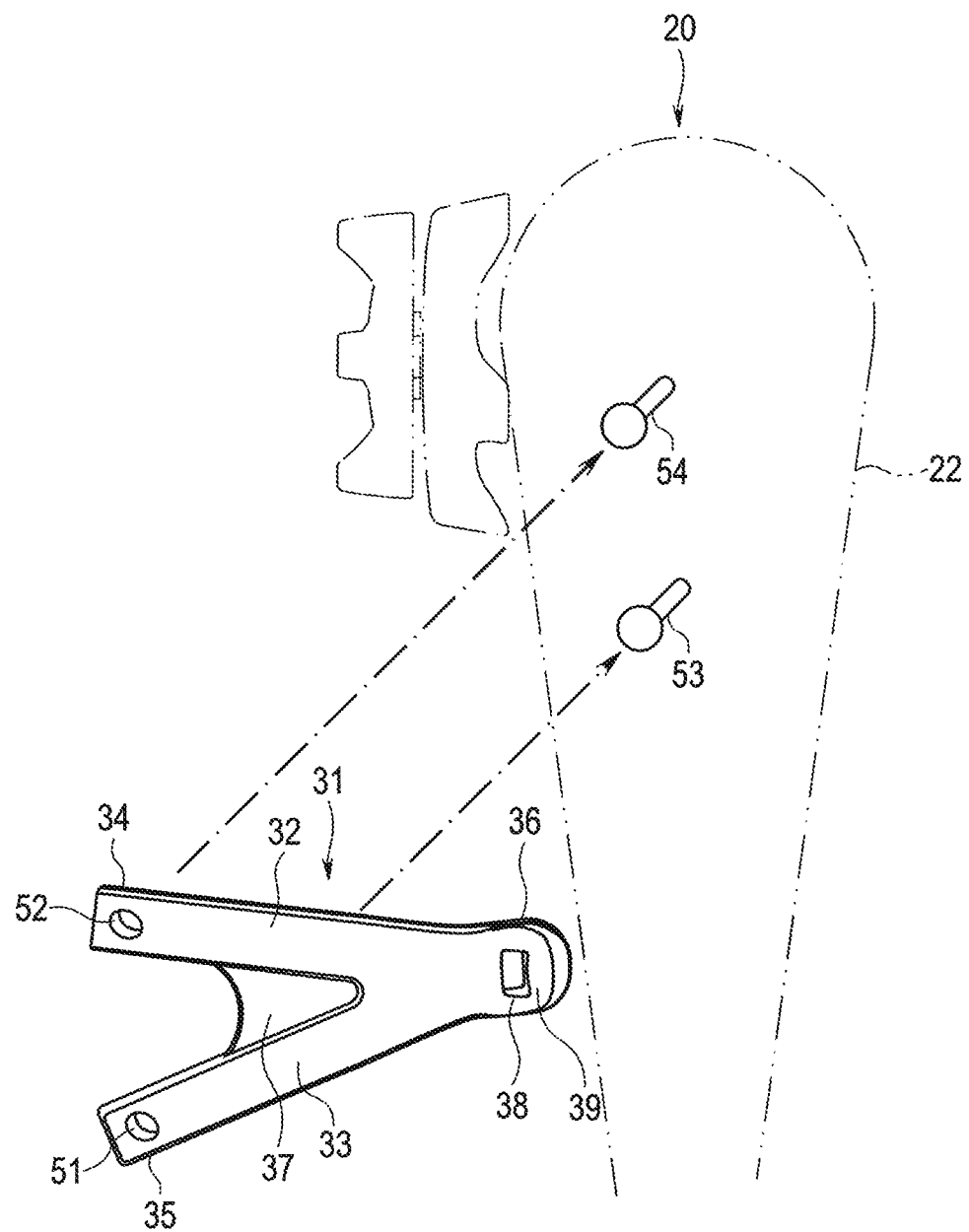
FIG. 15 is a perspective view showing a fixing band that is detachable from an operation portion of a baby endoscope according to a first modification.

FIG. 15 is a perspective view showing a fixing band that is detachable from an operation portion of a baby endoscope according to a first modification.

As shown in FIG. 15, a fixing band 31 may have a configuration in which hole portions 51 and 52 serving as locked portions are respectively provided at two end portions 34 and 35 of a first belt-like portion 32 and a second belt-like portion 33 separated from each other and are detachable from locking bodies 53 and 54 provided in an operation portion 22 of a baby endoscope 20 and serving as locking portions having a diameter-enlarged spherical head to be engaged with the hole portions 51 and 52.

With such a configuration, the baby endoscope 20 can be a reuse type that can be used repeatedly by being sterilized before and after use. The fixing band 31 may be a disposable type that is discarded after use or a reuse type that is reused by being sterilized after use.

(Second Modification)

Figure 16:
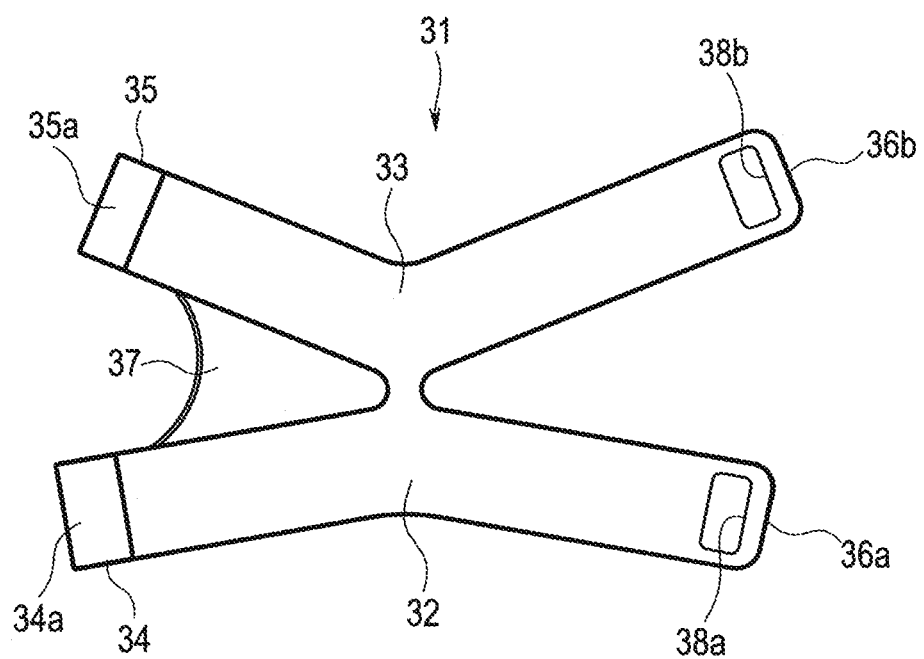
FIG. 16 is a plan view showing a configuration of a fixing band according to a second modification.

FIG. 16 is a plan view showing a configuration of a fixing band according to a second modification.

As shown in FIG. 16, a fixing band 31 has a substantially X-shape in which two end portions 36a and 36b separated away from two end portions 34 and 35 of a first belt-like portion 32 and a second belt-like portion 33 separated from each other are separated from each other. Locking holes 38a and 38b serving as locked portions are formed in the end portions 36a and 36b, respectively.

A baby endoscope 20 is fixed to an operation portion 12 of a mother endoscope 10 in a manner that the locking holes 38a and 38b of the end portions 36a and 36b are respectively hooked to two hook portions 41 (not shown) serving as locking portions provided on an operation portion 22.

In such a configuration, the baby endoscope 20 is held and fixed to the mother endoscope 10 at a total of four places (four points) including the two end portions 34 and 35 of the first belt-like portion 32 and the second belt-like portion 33 separated from each other and the two end portions 36a and 36b. Thus, the baby endoscope 20 can be fixed to the mother endoscope 10 more stably.

When the number of end portions is increased, the fixing band 31 can hold and fix the baby endoscope 20 to the mother endoscope 10 at four or more places, and can obtain a more stable fixing and holding force.

Another form of the fixing band 31 having an effect similar to the effect of the second modification shown in FIG. 16 may have a substantially X-shape in which two diverged belt-like portions respectively having two end portions 34 and 35 are merged into one, and then the merged belt-like portion diverges into two again so as to have two end portions 36a and 36b, respectively.

The mother-baby type endoscope including the mother endoscope 10 and the baby endoscope 20 is exemplified in the above-described embodiment, but without being limited thereto, the fixing band 31 may also be configured to fix medical devices, which are different from the endoscope and are, for example, a catheter and a treatment instrument support device used in an endoscopic submucosal dissection (ESD), to the endoscope.

The invention described in the embodiment above is not limited to the embodiment and the modifications, and various modifications can be made in the implementation stage without departing from the spirit of the invention. Furthermore, the embodiment and the modifications described above include various stages of the inventions, and various inventions may be extracted by appropriate combination of a plurality of components disclosed herein.

For example, even if some components are deleted from all the components shown in the embodiment, if the problem to be solved can be solved and the advantageous effects stated can be achieved, a configuration from which the components have been deleted can be extracted as an invention.

According to the present invention, it is possible to stably fix the medical device to be attached to the endoscope, and to realize the endoscope apparatus in which the medical device does not slip down and operability is improved.

What is claimed is:

1. An endoscope apparatus comprising:
an endoscope including a first operation portion coupled to a first insertion portion configured to be inserted into a subject;
a medical device including a second operation portion coupled to a second insertion portion configured to be inserted into the subject through the first insertion portion, the second operation portion including at least one locking member;
a bending operation member provided on the second operation portion, the bending operation member controlling a bending operation of the second insertion portion;
a concave portion formed on an exterior surface of the second operation portion, the concave portion being entirely formed on a side of the second operation portion that is opposite to the bending operation member, the side being opposite to the bending operation portion across a longitudinal axis of the second operation portion; and
a belt-like body having flexibility and including at least three end portions, at least one of the three end portions including a locked member to be locked to the locking member, the belt-like body being configured to be wound around the endoscope to hold and fix the second operation portion of the medical device to the first operation portion such that the concave portion of the second operation portion faces the first operation portion, in a state where the at least three end portions are connected to the second operation portion.

2. The endoscope apparatus according to claim 1, wherein the endoscope is a mother endoscope including a tube channel provided in the first insertion portion and the first operation portion, and the medical device is a baby endoscope of which the second insertion portion is inserted into the tube channel.

3. The endoscope apparatus according to claim 1, wherein the belt-like body has elasticity and is wound around the endoscope to hold and fix the medical device.

4. The endoscope apparatus according to claim 1, wherein
the first operation portion is provided with a coupling member with the first insertion portion, and
the medical device is held and fixed by the belt-like body being wound around the first operation portion such that the concave portion faces the coupling member.

5. The endoscope apparatus according to claim 1, wherein
the coupling member has a truncated cone shape, and
the belt-like body includes two belt-like portions that closely contact with different outer diameter portions of the coupling member.

6. The endoscope apparatus according to claim 5, wherein
the belt-like body has two end portions separated from each other, with a predetermined angle formed between respective longitudinal axes of the two belt-like portions, and the two end portions are fixed to the second operation portion.

7. The endoscope apparatus according to claim 1, wherein
the at least one locking member provided to the second operation portion includes three locking members,
the belt-like body is configured in which all of the at least three end portions include the locked member each locked to a respective one of the three locking members and detachably attached to the second operation portion.

8. A medical device including a device operation portion fixed to an endoscope operation portion provided on an endoscope, the device operation portion being coupled to an insertion portion configured to be inserted into a subject, the device operation portion being provided with at least one locking member, the medical device comprising:
   a bending operation member provided on the device operation portion, the bending operation member controlling a bending operation of the insertion portion;
   a concave portion formed on an exterior surface of the device operation portion, the concave portion being entirely formed on a side of the device operation portion that is opposite to the bending operation member, the side being opposite to the bending operation portion across a longitudinal axis of the device operation portion; and
   a belt-like body having flexibility and including at least three end portions, at least one of the three end portions including a locked member to be locked to the locking member, the belt-like body being configured to be wound around the endoscope to hold and fix the device operation portion to the endoscope such that the concave portion faces the endoscope operation portion, in a state where the at least three end portions are connected to the device operation portion.

\* \* \* \* \*